United States Patent [19]

Tsuchida et al.

[11] 4,393,135

[45] Jul. 12, 1983

[54] METHOD FOR PRODUCING L-GLUTAMIC ACID BY FERMENTATION

[75] Inventors: Takayasu Tsuchida, Kawasaki; Shigeru Nakamori, Yokohama, both of Japan

[73] Assignee: Ajinomoto Company Incorporated, Tokyo, Japan

[21] Appl. No.: 212,245

[22] Filed: Dec. 2, 1980

[30] Foreign Application Priority Data

Dec. 10, 1979 [JP] Japan ............................ 54-160117
Feb. 23, 1980 [JP] Japan ............................ 55-22062

[51] Int. Cl.³ ................... C12N 1/20; C12N 15/00; C12P 13/14; C12R 1/185
[52] U.S. Cl. ................... 435/110; 435/172; 435/253; 435/317; 435/848; 435/849
[58] Field of Search ............... 435/110, 172, 317, 848, 435/849, 253

[56] References Cited

U.S. PATENT DOCUMENTS

| 3,939,042 | 2/1976 | Nakayama et al. | 435/110 |
| 3,986,933 | 10/1976 | Maldonado et al. | 435/110 |
| 4,237,224 | 12/1980 | Cohen et al. | 435/849 X |
| 4,278,765 | 7/1981 | Debabov et al. | 435/172 |

FOREIGN PATENT DOCUMENTS

52-38088 3/1977 Japan ............................ 435/172
55-21763 2/1980 Japan ............................ 435/110

*Primary Examiner*—Esther M. Kepplinger
*Attorney, Agent, or Firm*—Oblon, Fisher, Spivak, McClelland & Maier

[57] ABSTRACT

An L-glutamic acid producing microorganism, which is obtained by incorporation into a host strain of the genus Escherichia of a hybrid plasmid having inserted therein a DNA fragment with genetic information controlling L-glutamic acid production, said fragment being derived from a donor strain of Escherichia which is capable of producing L-glutamic acid useful for the production of high levels of L-glutamic acid.

16 Claims, No Drawings

METHOD FOR PRODUCING L-GLUTAMIC ACID BY FERMENTATION

BACKGROUND OF THE INVENTION

1. Field of the Invention

The present invention relates to a method for producing L-glutamic acid by fermentation, and particularly relates to a method for producing L-glutamic acid with a microorganism constructed by a gene recombination technique.

2. Description of the Prior Art

Hitherto, many wild strains of the genera Brevibacterium and Corynebacterium have been known to produce L-glutamic acid in their culture medium. In order to improve the L-glutamic acid productivity, artificial mutants have been induced from the known L-glutamic acid-producing wild strains.

These L-glutamic acid-producing wild or mutant strains produce L-glutamic acid in a yield from 40% to 60% from glucose, sucrose, acetic acid or ethanol.

It has, however, become difficult to increase the yields of L-glutamic acid using the artificial mutation techniques. A need therefore, continues to exist for the development of novel microorganisms capable of producing L-glutamic acid in high yield.

SUMMARY OF THE INVENTION

It is therefore an object of the invention to provide a method for producing L-glutamic acid in high yields.

Other objects of the invention, which will hereinafter become more readily apparent, have been attained by providing:

A method for producing L-glutamic acid which comprises; culturing in a culture medium an L-glutamic acid producing microorganism which is obtained by incorporating into a recipient strains of the genus Escherichia, a hybrid plasmid having inserted therein a DNA fragment possessing genetic information related to L-glutamic acid production, which is derived from a donor strain of the genus Escherichia, and recovering the L-glutamic acid accumulated in the culture medium.

DETAILED DESCRIPTION OF THE PREFERRED EMBODIMENTS

The DNA-donor strain used to construct the L-glutamic acid producer of this invention is a microorganism of the genus Escherichia which is capable of producing L-glutamic acid.

Strains having higher productivity of L-glutamic acid are preferable as the DNA-donor.

The examples of preferred DNA-donor strain are mutants resistant to lysine-analogues, which can be obtained by conventional mutation techniques. The lysine-analogues are those which inhibit the growth of Escherichia strains, but the inhibition is suppressed partially or completely when L-lysine co-exists in the medium. Examples of lysine-analogues are oxa-lysine, lysine-hydroxamate, S-(2-aminoethyl)-cysteine (AEC), γ-methyl-lysine, and β-chloro-caprolactam.

Chromosomal DNA is extracted from the DNA-donor in a well known manner and treated with a restriction endonuclease by a well known method (Biochem. Biophys. Acta 383:457 (1975)). The plasmid or phage DNA used as the vector in the synthesis procedure is also treated with a restriction endonuclease in an analogous manner. Various kinds of restriction endonuclease can be used, if the digestion of the chromosomal DNA is done partially. Thereafter, the digested chromosomal DNA and vector are subjected to a ligation reaction.

Recombination of DNA to prepare the hybrid DNA can be carried out also by incorporating with terminal transferase deoxyadenylic acid and thymidylic acid, or deoxyguanylic acid and deoxycytidylic acid into the chromosomal DNA and vector DNA, and thereafter subjecting the modified DNAs to anealing.

As the vector, Col El, pSC 101, pBR 322, pACYC 177, pCRI, R6K and λ phage, and their derivatives are preferably used.

The recipient strain of the hybrid DNA is a microorganism of the genus Escherichia. When glutamic acid-requiring mutant is used as the recipient strain, it is convenient to distinguish a transformant having the productivity of L-glutamic acid from the recipient strains. Strains having higher productivity of L-glutamic acid, or L-glutamic acid requiring mutants derived from the strains having higher productivity of L-glutamic acid are desirably used as the recipient. In order to increase the productivity of L-glutamic acid of the recipient, resistance to chemical drugs such as p-fluorophenylalanine (FPA) S-(2-aminoethyl)-cysteine (AEC), 2-thiazolealanine (2TA), 1, 2, 4-triazolealanine (TRA), α-keto-malonic acid, fluoro-pyruvic acid and malonic acid is given to the microorganism of the genus Escherichia.

The hybrid DNA thus obtained can be incorporated into the recipient by a conventional transformation technique e.g. that described in J. Bacteriol., 119:1072 (1974). The desired transformant is screened using a medium on which only a clone, having one or both of the characteristics of L-glutamic acid productivity possessed by the chromosomal DNA fragment and those possessed by vector DNA, can grow.

The methods of culturing the L-glutamic acid producing strains thus obtained are conventional, and are similar to the methods for the cultivation of known L-glutamic acid producing microorganisms. Thus, the culture medium employed may be a conventional one containing carbon sources, nitrogen sources, inorganic ions and, when required, minor organic nutrients such as vitamins or amino acids. Examples of suitable carbon sources are glucose, sucrose, lactose, starch hydrolysate and molasses. Gaseous ammonia, aqueous ammonia, ammonium salts and other nitrogen containing materials can be used as the nitrogen source.

Cultivation of the recombinant microorganisms may be conducted under aerobic conditions, the pH and the temperature of the medium being adjusted to a suitable level and continued until the formation of L-glutamic acid ceases.

The L-glutamic acid accumulated in the culture medium can be recovered by conventional procedures.

By the method of the present invention, L-glutamic acid can be produced in higher yields than has been achieved by previously known methods using artificial mutants of Escherichia.

The invention will now be illustrated by the following Examples.

EXAMPLE 1

(1) Preparation of chromosomal DNA possessing genetic information related to L-glutamic acid production

*Escherichia coli* EG-19 (NRRL B-12282), a mutant resistant to AEC, derived from K-12 (ATCC 10798) by exposing K-12 cells to 250 μg/ml of N-methyl-N'-nitro-N-nitrosoguanidine in a citric acid buffer of pH 6.0 at 30° C. for 25 minutes and separating the colony which appeared on the agar medium, was cultured at 37° C. for 3 hours with shaking in 1 liter of L-medium containing 1 g/dl of peptone, 0.5 g/dl of yeast extract, 0.1 g/dl of glucose and 0.5 g/dl of NaCl (pH adjusted to 7.2), and bacterial cells in the exponential growth phase were harvested. Chromosomal DNA was extracted by a conventional phenol-method, and 3.4 mg of purified DNA was obtained.

(2) Preparation of vector DNA

As the vector, DNA of pBR 322 was prepared as follows. A strain of *Escherichia coli* K-12 harbouring the plasmid pBR 322 was incubated at 37° C. in 1 liter of a glucose-"casamino acid"-inorganic salts medium containing 2 g of glucose, 1 g of $NH_4Cl$, 6 g of $Na_2HPO_4$, 3 g of $KH_2PO_4$, 5 g of NaCl, 0.1 g of $MgSO_4 \cdot 7H_2O$, 0.015 g of $CaCl_2 \cdot 2H_2O$, 20 g of "casamino acid", and 100 μg of thiamine.HCl, each per liter (pH adjusted to 7.2). After the strain had been incubated until the late log phase, 170 μg/ml of chloramphenicol were added to the culture medium. By this process, the plasmid DNA was amplified and accumulated abundantly in the bacterial cells.

After 16 hours of incubation, cells were harvested and then lysed by treatment with lysozyme and SDS. The lysate was centrifuged at 30,000 xg for 1 hour to obtain a supernatant. After concentrating the supernatant, 480 μg of plasmid DNA was obtained by fractionation using cesium chloride-ethidium bromide equilibrium density gradient centrifugation.

(3) Insertion of chromosomal DNA fragment into the vector

10 μg of the chromosomal DNA was treated with the restriction endonuclease Hind III at 37° C. for 5, 10, 20, 30, and 60 minutes, respectively, to cleave the DNA chains, and then heated at 65° C. for 5 minutes. 10 μg of the vector DNA was also treated with the restriction endonuclease Hind III at 37° C. for 1 hour to cleave the DNA completely, and then heated at 65° C. for 5 minutes.

The digested chromosomal DNA solution and cleaved vector DNA solution were mixed and subjected to the ligation reaction of DNA fragments by a $T_4$ phage DNA-ligase in the presence of ATP and dithiothreitol at 10° C. for 24 hours. The reaction mixture was then heated at 65° C. for 5 minutes, and a two fold volume of ethanol was added to it. The precipitated recombinant DNA was recovered.

(4) Genetic transformation with the hybrid plasmid harbouring genetic information related to L-glutamic acid production A histidine requiring strain, *Escherichia coli* EHR-13 (NRRL 12283), which was derived from *Escherichia coli* K-12 by N-methyl-N'-nitro-N-nitrosoguanidine mutagenesis (250 μg/ml in a citric acid buffer, pH 6.0 at 30° C. for 25 minutes) was cultured in 10 ml of L-medium at 37° C. with shaking. Cells in exponential growth phase were harvested, and suspended in 0.1 M $MgCl_2$ solution and then in 0.1M $CaCl_2$ solution in an ice-bath, whereby "competent" cells having the ability of DNA uptake were prepared.

To the competent cells suspension, the hybrid plasmid DNA obtained in step (3), was added. The suspension was kept in an ice-bath for 30 minutes, then heated at 42° C. for 2 minutes, and again allowed to stand in an ice-bath for 30 minutes. The cells, thus being incorporated with the hybrid plasmid DNA, were inoculated into L-medium and the medium was shaken at 37° C. for 2 hours, whereby the transformation reaction was completed. The cells were harvested, washed, and resuspended. A small portion of the cell suspension was spread on an agar plate containing 2 g of glucose, 1 g of $(NH_4)_2SO_4$, 7 g of $K_2HPO_4$, 2 g of $KH_2PO_4$, 0.1 g of $MgSO_4 \cdot 7H_2O$, 0.5 g of sodium citrate.$2H_2O$, 0.1 g of L-histidine, 0.5 g of AEC.HCl, 20 mg ampicillin and 2 g of agar, each per liter (pH adjusted to 7.2). The plate was incubated at 37° C. for 3 days.

Colonies appearing on the plate were picked up and L-glutamic acid-producing, being resistant to AEC and L-histidine requiring transformants were selected. Thus NRRL B-12286 (AJ 11499, FERM-P 5301) was obtained as the best glutamic acid-producing transformant.

(5) Production of L-glutamic acid by the novel L-glutamic acid-producing strain The Table shows the experimental result of the fermentative production of L-glutamic acid using the strains NRRL B-12286, the DNA-donor strain EG-19, and the DNA-recipient EHR-13.

The fermentation medium contained 5 g/dl of glucose, 2.5 g/dl of ammonium sulphate, 0.2 g of $KH_2PO_4$, 0.1 g/dl of $MgSO_4 \cdot 7H_2O$, 0.05 g/dl of yeast extract, 1.0 mg/l of thiamine.HCl, 15 mg/dl of L-histidine, 1 mg/dl of $FeSO_4 \cdot 7H_2O$, 1 mg/dl of $MnSO_4 \cdot 4H_2O$ and 2.5 g/dl of $CaCO_3$ (separately sterilized) and the pH was adjusted to 7.0. Twenty milliliter batches of the fermentation medium were placed in 500 ml flasks, inoculated with one loopful inoculum of the test microorganism, and cultivation was carried out at 31° C. for 72 hours.

The amount of L-glutamic acid in the supernatant of the fermentation broth was determined by microbiological assay.

TABLE 1

| Microorganism | L-glutamic acid produced (mg/dl) |
|---|---|
| EG-19 | 154 |
| EHR-13 | 41 |
| NRRL B-12286 | 305 |

EXAMPLE 2

*Escherichia coli* K-12 was exposed to 250 μg/ml N-methyl-N'-nitro-N-nitrosoguanidine in a citric acid buffer of pH 6.0 at 30° C. for 25 minutes, and strain No. 283-5 (NRRL B-12295) which is resistant to FPA, strain No. 2-3 (NRRL B-12296) which is resistant to AEC, strain No. 12-3 (NRRL B-12297) which is resistant to 2TA, and No. 13-3 (NRRL B-12298) which is resistant to TRA were obtained, respectively.

The hybrid DNA obtained in step (3) of Example 1 were incorporated into No. 283-5, No. 2-3, No. 12-3 and No. 13-3 by the manner shown in step (4) of Example 1.

Thus, transformants having the productivity of L-glutamic acid, AJ 11545 FERM-P 5407 (NRRL B-12299), AJ 11546 FERM-P 5408 (NRRL B-12300), AJ 11547 FERM-P 5409 (NRRL B-12301), and AJ 11548 FERM-P 5410 (NRRL B-12302) were obtained from the recipients No. 283-5, No. 2-3, No. 12-3 and No. 13-3, respectively.

Productivity of L-glutamic acid of the transformants, the DNA donor strain EG-19, and the recipients was tested by the manner shown in step (5) of Example 1.

The results are shown in Table 2.

TABLE 2

| Strains tested | L-Glutamic acid accumulated (mg/dl) |
| --- | --- |
| EG-19 | 68 |
| No. 283-5 | 1,049 |
| No. 2-3 | 69 |
| No. 12-3 | 31 |
| No. 13-3 | 35 |
| AJ 11545 | 2,342 |
| AJ 11546 | 152 |
| AJ 11547 | 142 |
| AJ 11548 | 180 |

What is claimed is:

1. A method of producing L-glutamic acid by fermentation which comprises culturing in a culture medium an L-glutamic acid producing microorganism which is obtained by incorporating a hybrid plasmid having inserted therein a DNA fragment with genetic information controlling L-glutamic acid production, said fragment being derived from a donor strain of the genus Escherichia which is capable of producing L-glutamic acid, into a recipient strain of the genus Escherichia, wherein said L-glutamic acid producing microorganism is the transformant NRRL B-12286, NRRL B-12299, NRRL B-12300, NRRL B-12301, or NRRL B-12302.

2. The method of claim 1, wherein said donor strain is a mutant resistant to a lysine-analogue.

3. The method of claim 1, wherein said donor strain is a mutant resistant to oxa-lysine, lysine-hydroxamate, S-(2-aminoethyl)-cysteine, γ-methyl-lysine, or β-chloro-caprolactum.

4. The method of claim 1, wherein said recipient is a mutant resistant to p-fluorophenylalanine, S-(2-aminoethyl)-cysteine, 2-thiazolealanine, or 1, 2, 4-triazolealanine.

5. The method according to claim 1 wherein the L-glutamic acid producing microorganism is the transformant NRRL B-12286.

6. The method according to claim 5 wherein the transformant is resistant to S-(2-aminoethyl)-cysteine.

7. The method according to claim 1 wherein the L-glutamic acid producing microorganism is the transformant NRRL B-12299.

8. The method according to claim 1 wherein the L-glutamic acid producing microorganism is the transformant NRRL B-12300.

9. The method according to claim 1 wherein the L-glutamic acid producing microorganism is the transformant NRRL B-12301.

10. The method according to claim 1 wherein the L-glutamic acid producing microorganism is the transformant NRRL B-12302.

11. An L-glutamic acid producing transformant of the genus Escherichia containing a hybrid plasmid having inserted therein a DNA fragment with genetic information controlling L-glutamic acid production derived from a donor mutant of the genus Escherichia capable of producing L-glutamic acid, said mutant being resistant to lysine analog, wherein said transformant is NRRL B-12286, NRRL B-12299, NRRL B-12300, NRRL B-12301, or NRRL B-12302.

12. The transformant according to claim 11 having the designation NRRL B-12286.

13. The transformant according to claim 11 having the designation NRRL B-12299.

14. The transformant according to claim 11 having the designation NRRL B-12300.

15. The transformant according to claim 11 having the designation NRRL B-12301.

16. The transformant according to claim 11 having the designation NRRL B-12302.

* * * * *